(12) United States Patent
Sankai

(10) Patent No.: US 11,020,294 B2
(45) Date of Patent: Jun. 1, 2021

(54) MOBILITY AND MOBILITY SYSTEM

(71) Applicants: CYBERDYNE Inc., Tsukuba (JP); University of Tsukuba, Tsukuba (JP)

(72) Inventor: Yoshiyuki Sankai, Ibaraki (JP)

(73) Assignees: CYBERDYNE INC., Tsukuba (JP); UNIVERSITY OF TSUKUBA, Tsukuba (JP)

( * ) Notice: Subject to any disclaimer, the term of this patent is extended or adjusted under 35 U.S.C. 154(b) by 309 days.

(21) Appl. No.: 16/331,074

(22) PCT Filed: Apr. 4, 2017

(86) PCT No.: PCT/JP2017/014109
§ 371 (c)(1),
(2) Date: Mar. 6, 2019

(87) PCT Pub. No.: WO2018/047392
PCT Pub. Date: Mar. 15, 2018

(65) Prior Publication Data
US 2019/0192361 A1  Jun. 27, 2019

(30) Foreign Application Priority Data
Sep. 6, 2016 (JP) .............................. JP2016-173336

(51) Int. Cl.
*A61G 5/04* (2013.01)
*B62D 6/00* (2006.01)
(Continued)

(52) U.S. Cl.
CPC .............. *A61G 5/04* (2013.01); *A61B 5/1116* (2013.01); *A61B 5/4803* (2013.01);
(Continued)

(58) Field of Classification Search
CPC ........ A61G 5/04; G06K 9/00805; G06T 7/70; G06T 7/50; G06T 2207/30261;
(Continued)

(56) References Cited

U.S. PATENT DOCUMENTS

| 3,374,845 A | 3/1968 | Selwyn |
| 6,349,231 B1 * | 2/2002 | Musha ................... A61B 5/378 600/544 |

(Continued)

FOREIGN PATENT DOCUMENTS

| JP | 2002-197569 A | 7/2002 |
| JP | 2006-280511 A | 10/2006 |

(Continued)

OTHER PUBLICATIONS

Notice of Reasons for Refusal for related JP App No. 2018-538012 dated Feb. 25, 2020, 12 pages.
(Continued)

*Primary Examiner* — Ramsey Refai
(74) *Attorney, Agent, or Firm* — Procopio, Cory, Hargreaves & Savitch LLP

(57) ABSTRACT

Provided are a mobility and a mobility system which enable a person who requires nursing care with a deteriorated bodily function or cognitive function to lead a life with greater independence. The drive and travel of the mobility by the travel drive unit are controlled by adjusting the current travel state of the mobility to an optimal travel state for ensuring safety while reflecting the user's intention based on the current operation instruction detected by the operation unit, the command signal generated by the voluntary control unit, the travel environment sensed by the environment sensing unit, and the respective types of environmental information acquired by the information acquisition unit.

11 Claims, 11 Drawing Sheets

(51) Int. Cl.
*G05D 1/02* (2020.01)
*B62K 5/003* (2013.01)
*B60W 30/00* (2006.01)
*G06T 7/50* (2017.01)
*G06T 7/70* (2017.01)
*A61B 5/11* (2006.01)
*A61B 5/00* (2006.01)
*G06K 9/00* (2006.01)
*G10L 15/22* (2006.01)
*H04R 1/40* (2006.01)
*H04R 3/00* (2006.01)

(52) U.S. Cl.
CPC .......... *A61B 5/6894* (2013.01); *A61B 5/7455* (2013.01); *B60W 30/00* (2013.01); *B62D 6/00* (2013.01); *B62K 5/003* (2013.01); *G05D 1/02* (2013.01); *G05D 1/0248* (2013.01); *G06K 9/00805* (2013.01); *G06T 7/50* (2017.01); *G06T 7/70* (2017.01); *G10L 15/22* (2013.01); *H04R 1/406* (2013.01); *H04R 3/005* (2013.01); *G06T 2207/10024* (2013.01); *G06T 2207/30261* (2013.01)

(58) Field of Classification Search
CPC .......... G06T 2207/10024; H04R 1/406; H04R 3/005; A61B 5/6894; A61B 5/1116; A61B 5/4803; A61B 5/7455; G05D 1/0248; G01L 15/22
See application file for complete search history.

(56) References Cited

U.S. PATENT DOCUMENTS

| | | | |
|---|---|---|---|
| 6,636,763 B1* | 10/2003 | Junker | G06F 3/013 340/4.11 |
| 9,026,250 B2* | 5/2015 | Summer | A61G 5/1094 700/257 |
| 10,786,169 B2* | 9/2020 | Shin | A61B 5/681 |
| 2003/0192728 A1* | 10/2003 | Richey, II | A61G 5/045 180/204 |
| 2009/0005700 A1* | 1/2009 | Joshi | A61B 5/389 600/546 |
| 2011/0152709 A1 | 6/2011 | Yamada et al. | |
| 2012/0095633 A1 | 4/2012 | Kume et al. | |
| 2013/0096453 A1* | 4/2013 | Chung | G06F 3/04847 600/544 |
| 2013/0184980 A1 | 7/2013 | Ishikawa et al. | |
| 2015/0059086 A1 | 3/2015 | Clough | |

FOREIGN PATENT DOCUMENTS

| | | |
|---|---|---|
| JP | 2007-143886 A | 6/2007 |
| JP | 2010-119199 A | 5/2010 |
| JP | 2012-011886 A | 1/2012 |
| JP | 2012-106722 A | 6/2012 |
| JP | 2014-157478 A | 8/2014 |
| JP | 2014-206906 A | 10/2014 |
| JP | 2016-013214 A | 1/2016 |
| JP | 2016-084092 A | 5/2016 |
| WO | 2012/039280 A1 | 3/2012 |
| WO | 2015143273 A2 | 9/2015 |

OTHER PUBLICATIONS

Extended European Search Report for related EP App No. 17848339.2 dated Jun. 16, 2020, 7, pgs.

International Search Report for related International Application No. PCT/JP2017/014109, dated May 16, 2017; English translation provided; 9 pages.

* cited by examiner

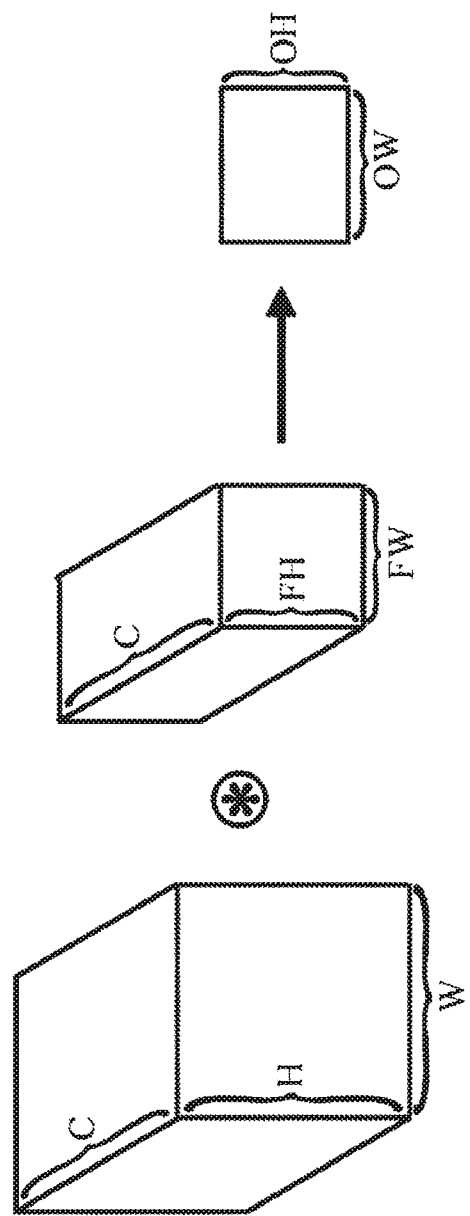

FIG.6

| Trial | Recognition rate [%] | | |
|---|---|---|---|
| | Bed | Desk | Chair |
| 1 | 100 | 0 | 0 |
| 2 | 100 | 0 | 0 |
| 3 | 100 | 0 | 0 |
| 4 | 100 | 0 | 0 |
| 5 | 100 | 0 | 0 |
| 6 | 100 | 0 | 0 |
| 7 | 100 | 0 | 0 |
| 8 | 100 | 0 | 0 |
| 9 | 99.9 | 0 | 0.01 |
| 10 | 100 | 0 | 0 |
| 11 | 100 | 0 | 0 |
| 12 | 100 | 0 | 0 |
| 13 | 99.5 | 0 | 0.05 |
| 14 | 100 | 0 | 0 |
| 15 | 100 | 0 | 0 |

FIG.7

| Trial | Recognition rate [%] | | |
|---|---|---|---|
| | Bed | Desk | Chair |
| 1 | 4.2 | 95.8 | 0 |
| 2 | 0 | 100 | 0 |
| 3 | 31.6 | 68.4 | 0 |
| 4 | 0.5 | 99.5 | 0 |
| 5 | 2.6 | 96 | 1.4 |
| 6 | 0 | 99 | 0 |
| 7 | 1.5 | 98.5 | 0 |
| 8 | 6.7 | 93.3 | 0 |
| 9 | 28.1 | 71.9 | 0 |
| 10 | 0.5 | 99.5 | 0 |
| 11 | 1.6 | 98.4 | 0 |
| 12 | 6.5 | 93.5 | 0 |
| 13 | 20.8 | 79.2 | 0 |
| 14 | 16.1 | 83.9 | 0.1 |
| 15 | 6.5 | 93.5 | 0 |

FIG.8

| Trial | Recognition rate [%] | | |
|---|---|---|---|
| | Bed | Desk | Chair |
| 1 | 0.3 | 0 | 99.7 |
| 2 | 0.2 | 4.1 | 95.8 |
| 3 | 0 | 0 | 99.9 |
| 4 | 24.9 | 0.5 | 74.6 |
| 5 | 0 | 2.4 | 97.6 |
| 6 | 0 | 0 | 100 |
| 7 | 17.7 | 0.1 | 82.2 |
| 8 | 0.1 | 0 | 99.9 |
| 9 | 0 | 0 | 100 |
| 10 | 8.7 | 0.7 | 90.6 |
| 11 | 0 | 0 | 100 |
| 12 | 2.1 | 0.2 | 97.7 |
| 13 | 0.2 | 0.2 | 99.6 |
| 14 | 2.7 | 0.1 | 97.2 |
| 15 | 0 | 0 | 100 |

MOBILITY AND MOBILITY SYSTEM

CROSS-REFERENCE TO RELATED APPLICATIONS

This application is a U.S. National Stage entry of PCT Application No: PCT/JP2017/014109 filed Apr. 4, 2017, which claims priority to Japanese Patent Application No. 2016-173336, filed Sep. 6, 2016, the contents of which are incorporated herein by reference.

TECHNICAL FIELD

The present invention relates to a mobility and a mobility system, and in particular can be suitably applied to a personal mobility capable of moving in the intended direction according to the user's operation.

BACKGROUND ART

In recent years, increase in the number of persons who require nursing care who have trouble going to the restroom, kitchen or shopping center due to the deterioration of their bodily function or cognitive function is now a major social issue of Japan that is encountering a super-aging society. Thus, development of a means for supporting their movement so they can lead a more independent life is being earnestly desired.

Conventionally, numerous proposals have been made for collision safety technologies to cover the insufficient recognition of obstacles in cases where a person who requires nursing care personally operates an electric wheelchair. For example, proposed is a technology of determining the possibility of collision of a vehicle body and an obstacle based on the position of the obstacle and the predicted passing area of the vehicle body, and correcting the speed and advancing direction of the vehicle body when it is determined that there is a possibility of collision when the vehicle body passes near the obstacle on the one hand, and maintaining the speed of the vehicle body when it is determined that there is no possibility of collision on the other hand (refer to PTL 1).

Moreover, proposed is a technology of determining whether an obstacle and a mobile object will approach each other within a predetermined distance and, when it is determined that they will come close to each other, planning the avoidance operation of the mobile object and the avoidance operation expected by the obstacle, whereby an avoidance operation that is more efficient in comparison to a case where the mobile object unilaterally avoids the obstacle is enabled (refer to PTL 2).

Furthermore, proposed is a technology of safely performing automatic avoidance even when there is an obstacle in the operated direction by creating a search region which extends in the operated direction of a vehicle body and which is substantially equal to the width of a vehicle body, and changing the search region into a tapered shape in the operated direction when the size of the operation input or the size of the operating force calculated from the operated direction and the operation input is great (refer to PTL 3).

CITATION LIST

Patent Literature

[PTL 1] Japanese Patent Application Publication No. 2012-11886
[PTL 2] International Publication No. 2012/039280
[PTL 3] Japanese Patent Application Publication No. 2012-106722

SUMMARY OF THE INVENTION

Problems to be Solved by the Invention

However, when the deterioration in the bodily function or cognitive function of a person who requires nursing care is advanced, it is extremely difficult for such person to personally operate an electric wheelchair and travel merely by mounting an automatic obstacle avoidance function, and this is practically insufficient in terms of independence.

In order to resolve the foregoing problem, considered may be a method of installing various sensors at various locations in the surrounding environment of the operator's travel route and safely guiding the operator's electric wheelchair to the destination. Nevertheless, by merely installing numerous sensors in the surrounding environment and safely guiding the operator's electric wheelchair, while it may be possible for the operator to independently use the electric wheelchair and ensure the operator's safety, there is a possibility that hardly any consideration will be given to the operator's independence.

The present invention was devised in view of the foregoing points, and an object of this invention is to propose a mobility and a mobility system which enable a person who requires nursing care with a deteriorated bodily function or cognitive function to lead a life with greater independence.

Means to Solve the Problems

In order to achieve the foregoing object, the present invention provides a mobility including an operation unit which detects an operation instruction input by a user, and a travel drive unit which drives and causes the mobility to travel at a travel speed and in a travel direction according to the operation instruction detected by the operation unit, comprising: a biosignal detection unit including an electrode for detecting a biosignal of the user from the user's finger which comes into contact with the operation unit; a voluntary control unit which generates a command signal for causing the travel drive unit to generate power according to the user's intention based on the biosignal acquired by the biosignal detection unit; an environment sensing unit which enables the mobility body side to sense a travel environment during travel; an information acquisition unit which acquires at least one or more types of environmental information presented from an external environment; a travel adjustment unit which adjusts a current travel state of the mobility to an optimal travel state for ensuring safety while reflecting the user's intention based on the current operation instruction detected by the operation unit, the command signal generated by the voluntary control unit, the travel environment sensed by the environment sensing unit, and the respective types of environmental information acquired by the information acquisition unit; and a travel control unit which controls the drive and travel of the mobility by the travel drive unit so as to attain the travel state adjusted by the travel adjustment unit.

According to the foregoing mobility, even if the user is a person who requires nursing care with a deteriorated bodily function or cognitive function, by adjusting the current travel state of the mobility to an optimal travel state for ensuring safety while reflecting the user's intention, the user can travel in one's intended direction with a sense of security, even without the support of a third party, on the premise of following one's own intention to the extent possible.

The mobility of the present invention further comprises a posture sensing unit which is provided at a support part for supporting a weight of the user and senses a body motion change and a gravity center change of the user, wherein the travel adjustment unit adjusts the travel state by reflecting the weight shift and the gravity center change detected by the posture sensing unit in the current operation instruction detected by the operation unit.

Consequently, by reflecting the user's weight shift and gravity center change in addition to the current operation instruction by the user, it will be possible to approximate the user's intended travel state.

The mobility of the present invention further comprises a speech analysis unit which analyzes a spoken content based on the user's voice collected via a directional microphone, wherein the travel adjustment unit adjusts the travel state by reflecting the analysis result of the speech analysis unit in the current operation instruction detected by the operation unit.

Consequently, by reflecting the spoken content related to travel instructions among the user's spoken content in addition to the current operation instruction by the user, it will be possible to approximate the user's intended travel state.

The mobility of the present invention further comprises a physiological state detection unit which detects a physiological state of the user, wherein, when the physiological state detected by the physiological state detection unit is outside of a predetermined standard range for a predetermined time or longer, the travel adjustment unit adjusts the current travel state of the mobility to a travel state which gives priority to ensuring safety irrespective of the current operation instruction detected by the operation unit.

Consequently, if it is determined that the user's physiological state is inferior and may impair the travel and movement of the mobility, it will be possible to avoid any subsequent risks by forcibly guiding the mobility to a place where safety can be ensured. By simultaneously warning those around the mobility by emitting an emergency alert from a speaker provided to the mobility or sending emergency information to a portable terminal held by the user's interested party via a communication function, the function for protecting the user can be fulfilled.

Furthermore, with the mobility of the present invention, the environment sensing unit includes an imaging unit which captures images of a target object from a plurality of different viewpoints, and the travel adjustment unit recognizes the target object based on RGB data, which is an imaging result of the imaging unit, and determines whether the target object which has approached to be within a predetermined target distance is an obstacle while calculating a relative position of the target object and the mobility body based on depth data calculated from the RGB image data.

Consequently, the mobility can recognize whether the approaching target object is an obstacle according to the circumstances and generate a safe travel path and engage in autonomous travel based on the relative position of the target object and the mobility body.

The mobility of the present invention further comprises an information content notification unit which notifies the user, in real time, either one or both of a content of adjustment and a fact of adjustment of the travel state adjusted by the travel adjustment unit. Furthermore, the information content notification unit is configured from a stimulation application unit which applies physical stimulation to the user according to the content of adjustment of the travel state adjusted by the travel adjustment unit.

Consequently, the user can recognize the content of adjustment or fact of adjustment of the travel state in the form of feedback, and acquire a learning effect based on function recovery by being aware of the difference between one's own operation instruction and the adjustment that was made.

The present invention additionally provides a mobility system including the foregoing mobility, and an environmental information presentation unit which presents at least one or more types of environmental information to the mobility, wherein the environmental information presentation unit comprises an information presentation unit which is provided for each type of environmental information and presents corresponding environmental information in response to a request from the mobility, and wherein the information acquisition unit of the mobility only acquires utilizable environmental information from each of the information presentation units.

Consequently, with the mobility system, by acquiring the ambient environmental information as needed while the mobility is traveling, the autonomous control ability of the mobility itself can be supplemented with the information content based on the environmental information. By coordinating the user's environment recognition ability with the environmental information presentation unit located in the mobility's external environment, it will be possible to realize travel control that is much safer for the user.

Furthermore, with the mobility system of the present invention, the mobility comprises an information communication unit which externally transmits the content of adjustment of the travel state adjusted by the travel adjustment unit together with at least one or more among a weight shift and a gravity center change detected by the posture sensing unit, a cognitive ability sensed by the cognitive ability sensing unit, and a physiological state detected by the physiological state detection unit, and the mobility system further comprises a data terminal device which is provided separately from the mobility, receives various types of information sent from the information communication unit, and sends the received information to a management server via a communication line.

Consequently, with the mobility system, the user's bodily function and cognitive function can be accumulated in the management server via an external data terminal device based on the content of adjustment of the user's travel state generated from the information communication unit and the various types of information representing the corresponding bodily function and cognitive function. Furthermore, by analyzing, in chronological order, the user's information accumulated in the management server, it will be possible to comprehend the level of deterioration in the bodily function and cognitive function.

Furthermore, with the mobility system of the present invention, the mobility further comprises a position information detection unit which detects position information of the mobility, and the information communication unit transmits the current position information obtained from the position information transmission unit. Consequently, the external data terminal device will also be able to constantly confirm the position information of the mobility.

Furthermore, with the mobility system of the present invention, the data terminal device sends a command signal representing an operation command which was externally input to the mobility, and, upon receiving the command signal via the information communication unit, the operation adjustment unit of the mobility preferentially switches to a travel state according to the operation command based on the command signal irrespective of the current operation instruction.

Consequently, with the mobility system, when the administrator using the data terminal device wishes to bring over the mobility in cases where there is concern regarding the health of the user riding the mobility, the administrator can change the destination of the mobility to one's own location and forcibly operate and cause the mobility to travel to one's own location. Otherwise, as a result of the administrator, who is using the data terminal device, remotely controlling the mobility, it will be possible to sufficiently ensure safety even when the user riding the mobility is a person who requires nursing care.

Advantageous Effects of the Invention

According to the present invention, it is possible to realize a mobility and a mobility system which enable a user, even in cases of becoming a person who requires nursing care due to the deterioration in such person's bodily function or cognitive function, to lead a life with greater independence by performing travel control while coordinating with the information content acquired from the external environment, without limitation to the operation instruction according to the user's intention.

BRIEF DESCRIPTION OF DRAWINGS

FIG. 3A is a conceptual diagram explaining the convolution layer and the pooling layer of the convolutional neural network.

FIG. 6 is a diagram showing the recognition result of the bed.

FIG. 7 is a diagram showing the recognition result of the desk.

FIG. 8 is a diagram showing the recognition result of the chair.

DESCRIPTION OF EMBODIMENTS

An embodiment of the present invention is now explained in detail with reference to the appended drawings.

(1) Configuration of Mobility System According to This Embodiment

Figure 1:
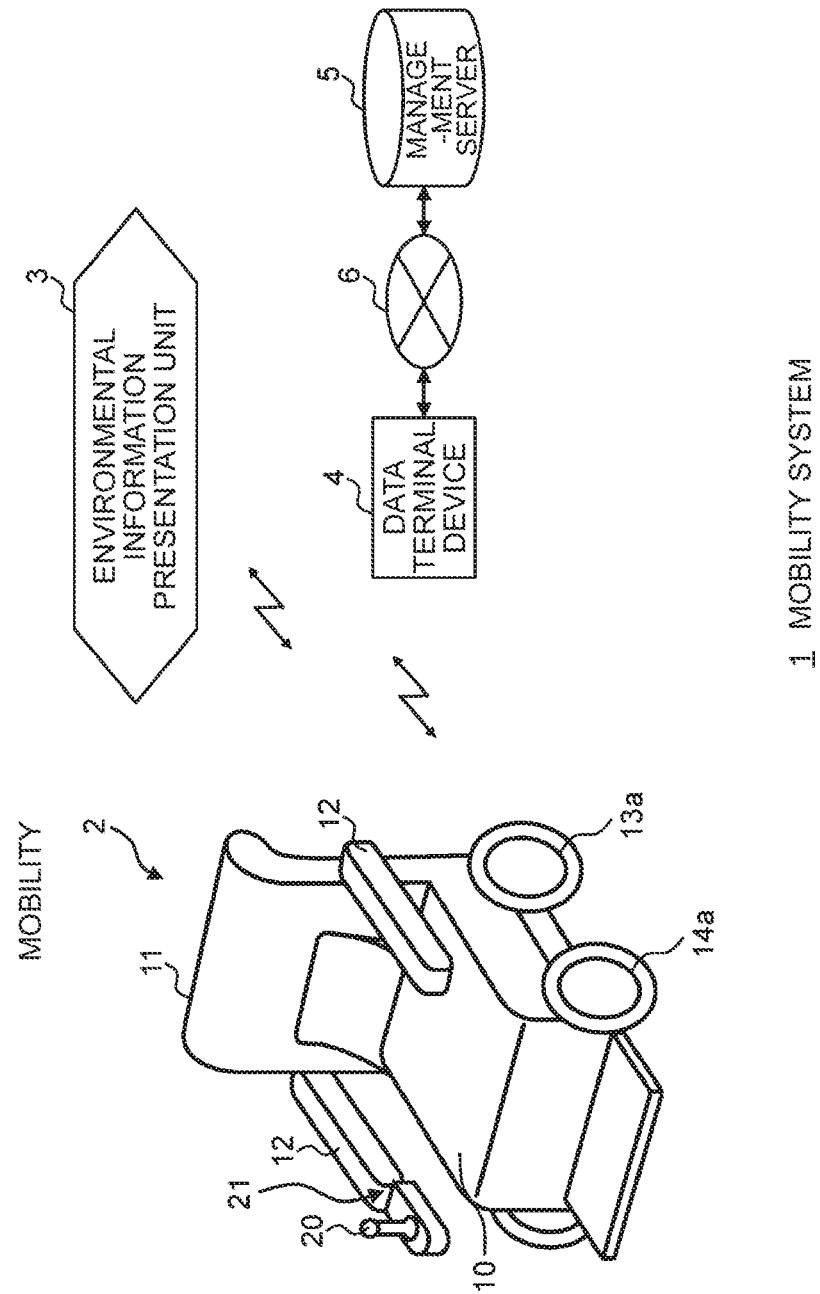
FIG. 1 is a conceptual diagram showing the overall configuration of the mobility system according to an embodiment of the present invention.

As shown in FIG. 1, a mobility system 1 according to the present invention includes a mobility 2 which travels at a travel speed and in a travel direction according to the user's operation, and an environmental information presentation unit 3 which presents at least one or more types of environmental information to the mobility 2. The mobility system 1 may also include a data terminal device 4 and a management server 5 which bi-directionally send and receive various types of data to and from the mobility 2.

The environmental information presentation unit 3 according to the present invention is configured to supplement the autonomous control ability of the mobility itself with the information content based on the environmental information by presenting environmental information to the mobility 2 from the outside. In other words, by coordinating the user's environment recognition ability with the environmental information presentation unit located in the external environment of the mobility 2, it will be possible to realize travel control that is much safer for the user.

As the environmental information, used may be various types of information for improving the user's environment recognition level and realizing safer travel to the destination. For example, used may be shortcut information to the destination, road surface condition (whether the road is flat, etc.) of the travel environment, route information capable of avoiding harm during rain, prior notice of the traffic volume and traffic state until reaching an intersection, prior notice of obstacles and the crossing of pedestrians, position information of restrooms and rest houses for wheelchairs, and store information of stores located in the travel environment.

The environmental information provision unit 3 provides the foregoing environmental information to the mobility 2 in the form of vision information, electromagnetic information, radio wave information, optical information and sound information via a provision means corresponding to each type of information in response to a request from the mobility 2 or automatically upon nearing the target location.

Specifically, as vision information, used may be a recognition pattern, landmark, licensing mark, QR code (registered trademark) installed in the floor, walls, ceiling or objects in the travel environment, or hologram. As the means for providing vision information, used may be an imaging camera or a 3D distance image sensor.

Moreover, as electromagnetic information or radio wave information, used may be RFID (Radio Frequency Identification) embedded in the travel environment, electric cable which generates a magnetic field, or GPS (Global Positioning System). As a means for providing such information, used may be an active-type or passive-type wireless communication means or infrared communication means.

Furthermore, as optical information, used may be a laser scanning range sensor, optical communication cord, or mechano-optical guide (irradiating the floor, wall or ceiling with optical information by using a laser pointer or the like). As a means for providing such information, used may be an imaging element such as a CMOS (complementary metal oxide semiconductor) image sensor, or a photoelectric conversion element such as a photoconductive light-receiving element or a photovoltaic light-receiving element.

Furthermore, as sound information, used may be original sound information generated from the user or surrounding environment, processed frequency information or pattern speech information (including abnormal noises as needed). As a means for providing such information, used may be a directional microphone or an omnidirectional microphone.

Accordingly, the mobility 2 integrally processes, communicates, and automatically determines a plurality of types of information that can be acquired from the environmental information presentation unit 3, and performs travel control while coordinating the acquired information with the operation instruction according to the user's intention.

(2) Configuration of Mobility According to This Embodiment

The mobility 2, as shown in FIG. 1, is a two-wheel drive four-wheel mobile object capable of traveling according to external operations or autonomously, and comprises a seat part (support part) 10 on which the user will sit, a backrest part 11 for supporting the user's back, and an armrest part 12 for supporting the user's arms.

A travel drive unit 15 configured from a pair of left and right driving rear wheels 13a, 13b on the rear side and a pair of left and right front wheels 14a, 14b on the front side is provided below the seat part 10. The left and right driving rear wheels 13a, 13b in the travel drive unit 15 are respectively and independently rotatably driven, and the mobility 2 moves forward or backward based on the forward rotation or backward rotation of the driving rear wheels 13a, 13b, and turns right or left while moving forward by imparting a difference in the forward rotating speed of the driving rear wheels 13a, 13b. Moreover, the mobility 2 turns in its position by the driving rear wheels 13a, 13b being rotatably driven in mutually opposite directions.

The armrest part 12 is the part where the user places one's elbow upon sitting on the seat part 10. An operation unit 20 is provided to one of the armrest parts 12 (right-side armrest part 12). The operation unit 20 is configured, while not shown, such that a rod-shaped operation lever is pivotally supported, in a freely tiltable manner in the intended direction, by a bearing part provided to the front edge side, and the travel drive unit 15 is operated according to the tilt angle and the tilt direction of the operation lever operated by the user. The travel drive unit 15 independently drives the left and right driving rear wheels according to the operation instruction (direction and speed) that is input by the operation unit 20.

Moreover, a biosignal detection unit 21 (described later with reference to FIG. 2) having an electrode for detecting a biosignal in advance is mounted on the part where the user's finger comes into contact with the operation unit 20 in the chair part 12, and, based on the detected biosignal, the integrated control unit 30 described later (FIG. 2) generates a command signal for causing the travel drive unit 15 to generate power according to the user's intention.

The term "biosignal" as used in the present invention is a signal resulting from the electricity generated within the user's body, and is a signal that can be measured from the user's body and which changes chronologically pursuant to body movement or signals from the brain. For example, a biosignal refers to a signal generated based on biological activity such as a nerve potential or myogenic potential, brain waves, cardiac potential, or potential generated from a motion artifact (influence of motion), potential generated from biochemical reaction, or vibration such as pulse waves generated from pulsation of the heart.

The biosignal detection unit 21 according to the present invention has the same configuration and adopts the same principle as the subject matter described in Patent Registration No. 5409637 by the present inventors. Moreover, as a method of acquiring a signal for causing the user's finger to move, the motion aid described in Patent Registration No. 5472680 by the present inventors may be applied.

The front edge of the armrest part 12 is provided with a laser range sensor 31 which senses obstacles in the obliquely forward direction and the left and right direction, an RGB-D sensor 32 capable of 3D scanning, a 3D distance image sensor 33 and an imaging camera 34.

Specifically, the laser range sensor 31 irradiates the object (obstacle) viewed from the installation position with a laser, and receives the reflected light to calculate the distance. By measuring the distance at a given angular interval, it is possible to obtain fan-like distance information on a plane in a range of up to 30 m and an angle of 240 degrees.

Moreover, in addition to an RGB color camera function, the RGB-D sensor 32 has a depth sensor capable of measuring the distance to the object (obstacle) viewed from the camera, and is able to three-dimensionally scan the object. The depth sensor is configured from an infrared sensor, captures the image of the target in a state where a single pattern of structured light is projected on the object, and calculates the depth of the respective points on the image based on triangulation using the parameters thereof.

For example, when Kinect (trademark of Microsoft) is adopted as the RGB-D sensor 32, it is possible to capture images at a horizontal viewing angle of 57 degrees, a vertical viewing angle of 43 degrees, and a sensor range of 1.2 m to 3.5 m, and the RGB image can be acquired with 640×480 pixels and the depth image can be acquired with 320×240 pixels at 30 frames/second.

The reason why the RGB-D sensor 32 is installed at the front edge of the armrest part 12 is because it is not possible to ensure a vertical viewing angle with the travel drive unit which is close to the floor surface, and it is necessary to secure a height of 0.6 m to 1.8 m from the floor surface.

The 3D distance image sensor 33 irradiates LED pulses and, by measuring the arrival time of the reflected light from the object in pixel units and simultaneously superimposing the acquired image information, calculates the distance information to the object in pixel units. The 3D distance image sensor 33 has a detection ability that has a higher degree of accuracy than the foregoing RGB-D sensor 32, and, because the viewing angle is broader than that of the laser range sensor 31, it is necessary as an outdoor supplementary sensor.

For example, when Pixel Soleil (product name of Nippon Signal Co., Ltd.) is adopted as the 3D distance image sensor 33, it is possible to capture images at a horizontal viewing angle of 72 degrees, a vertical viewing angle of 72 degrees, and a sensor range of 0.3 m to 4.0 m.

With the mobility 2 of the present invention, the laser range sensor 31, the RGB-D sensor 32 and the 3D distance image sensor 33 are used to realize the SLAM (Simultaneous Localization and Mapping) technology of estimating one's own position relative to the external environment and simultaneously creating an environmental map.

The mobility 2 using the SLAM technology is able to identify its own travel path and autonomously move within the environment by dynamically creating an environmental map which represents the three-dimensional position of objects existing in real space while estimating its own position with a high degree of accuracy.

Furthermore, a directional microphone 35 and a speaker 36 are mounted at the upper center part of the backrest part 11 for collecting sounds of the surrounding environment and vocalizing messages or emitting warning sounds as needed.

(3) Internal Circuit Configuration of Mobility

Figure 2:
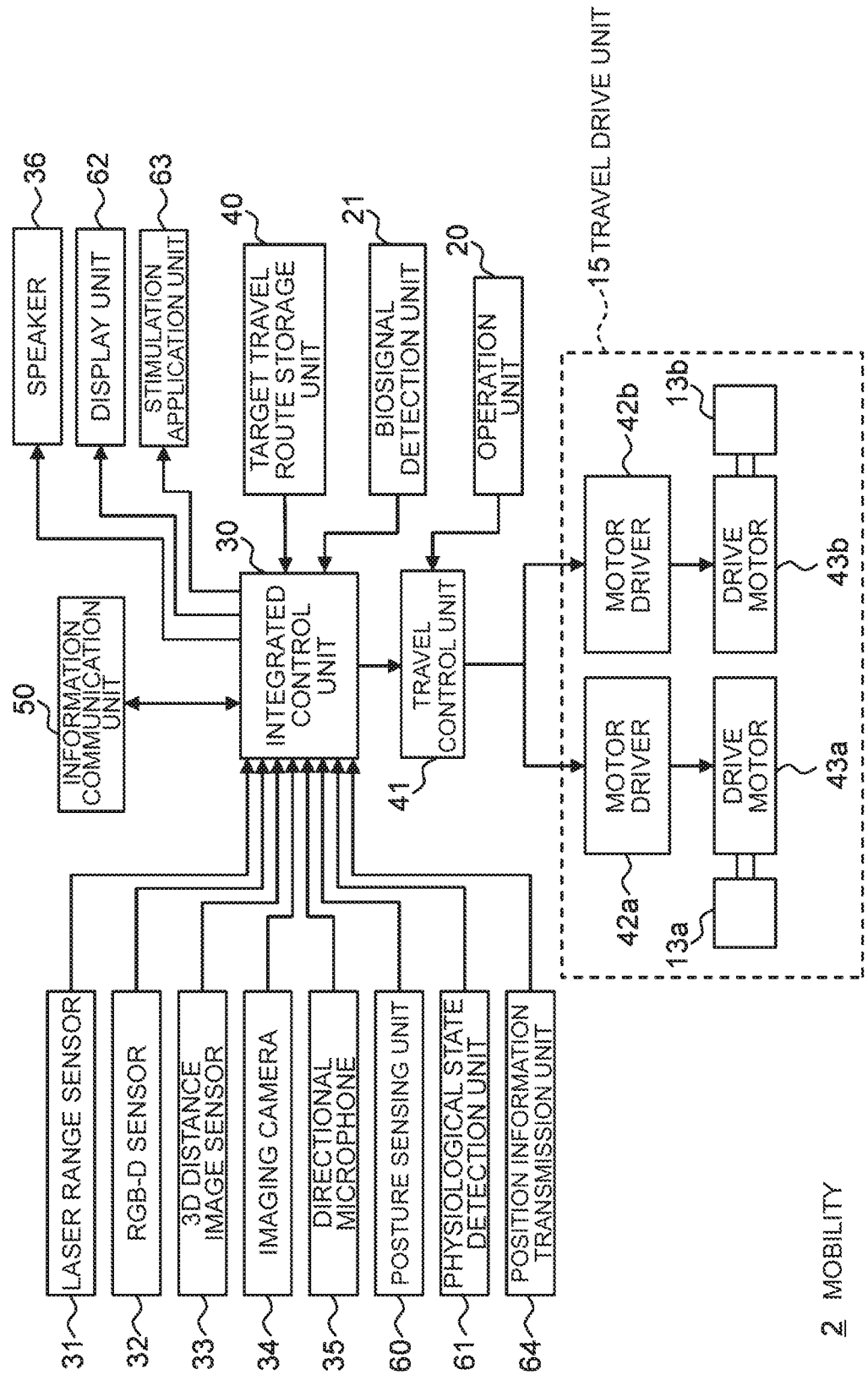
FIG. 2 is a block diagram showing the configuration of the control system of the mobility according to an embodiment of the present invention.

FIG. 2 is a configuration diagram of the control system installed in the mobility 2. The mobility 2 comprises an integrated control unit (travel adjustment unit) 30 which governs the control of the overall mobility 2, a target travel route storage unit 40 which stores travel route information, and a travel control unit 41 which controls the travel drive unit 15 according to the input from the operation unit 20 or the control performed by the integrated control unit 30.

The integrated control unit 30, while simultaneously estimating its own position and creating the environmental map described later based on the travel route information from the target travel route storage unit 40, which stores pre-set travel route information, and the respective detection signals from the laser range sensor 31, the RGB-D sensor 32 and the 3D distance image sensor 33, determines the suitability of the travel route or the necessity to change the travel route, and determines the existence of any obstacles on the travel route.

For example, the integrated control unit 30 determines whether the mobility 2, which is traveling on a road, will come into contact with an obstacle such as a roadside curbstone along the travel route, stops immediately before coming into contact with the obstacle, and changes the travel direction to the user's tracking direction. The integrated control unit 30 sends the determined travel route information to the travel control unit 41, and the travel control unit 41 controls the left and right motor drivers 42a, 42b and controls the rotation of the drive motors 43a, 43b according to the travel route information.

In effect, the mobility 2 uses the foregoing SLAM technology and automatically creates an environmental map of the travelable target areas within the actual environment, such as sidewalks, within a predetermined area.

Specifically, the mobility 2 creates an environmental map indicating the overall intended target area while setting, as an area representing the mobile environment, a local map on a grid partitioned with a two-dimensional lattice based on the distance information and the angle information relative to the object which are obtained from the laser range sensor 31 and the 3D distance image sensor 33. Simultaneously, the mobility 2 calculates its own travel distance based on the rotation angle read from an encoder (not shown) corresponding to the pair of driving rear wheels 13a, 13b of the mobility 2, and estimates its own position from the matching of the subsequent residential map and the environmental map created up to that point in time and its own travel distance.

Moreover, the mobility 2 comprises an information communication unit 50 which engages in wireless communication with the data terminal device 4, and, under the control of the integrated control unit 30, sends to the data terminal device 4 the content of adjustment of the travel state described later and various types of information representing the bodily function and cognitive function, and the foregoing content of adjustment and various types of information are sent from the data terminal device 4 and accumulated in the management server 5 via the communication line 6 (FIG. 1).

Furthermore, the mobility 2, by acquiring as much as possible environmental information from the information communication unit 50, the imaging camera 34, the directional microphone 35, the laser range sensor 31, the RGB-D sensor 32 and the 3D distance image sensor 33 as the available means within the environmental information presentation unit 3, can complement the autonomous control ability of the mobility itself with the information content based on the surrounding environmental information as needed while traveling. By coordinating the user's environment recognition ability with the environmental information presentation unit 3 located in the external environment of the mobility 2, it will be possible to realize travel control that is much safer for the user.

Moreover, the integrated control unit 30 generates a command signal for causing the travel drive unit 15 to generate power according to the user's invention based on the user's biosignal acquired by the foregoing biosignal detection unit 21.

The integrated control unit 30 adjusts the current travel state of the mobility 2 to an optimal travel state for ensuring safety while reflecting the user's invention based on the current operation instruction detected by the operation unit 20, the command signal generated as a result of voluntary control, the travel information sensed by the foregoing SLAM technology, and the environmental information acquired by the environmental information presentation unit 3. The travel control unit 41 drive-controls the motor drivers 42a, 42b of the travel drive unit 15 so as to attain the travel state adjusted by the integrated control unit 30.

Accordingly, with the mobility 2, even if the user is a person who requires nursing care with a deteriorated bodily function or cognitive function, by adjusting the current travel state of the mobility 2 to an optimal travel state for ensuring safety while reflecting the user's intention, the user can travel in one's intended direction with a sense of security, even without the support of a third party, on the premise of following one's own intention to the extent possible.

Moreover, the mobility 2 is provided with a posture sensing unit 60 configured by a plurality of pressure sensors being arranged in a two-dimensional matrix shape on the seat surface of the seat part 10, and the posture sensing unit 60 calculates the barycentric interface pressure based on the interface pressure distribution when the user sits on the seat surface of the seat part 10, and senses the user's weight shift and gravity center change.

In other words, the posture sensing unit 60 calculates the barycentric coordinates of the X-axis direction (left and right direction) and the Y-axis direction (front and back direction) in a two-dimensional array from the sum of all interface pressure data based on the interface pressure data sensed by the plurality of pressure sensors, and thereafter calculates the barycentric interface pressure of the seat surface based on the relation relative to the distance between the sensors. Furthermore, the posture sensing unit 60 obtains the user's body motion change and gravity center change based on the chronological data of the change in the barycentric interface pressure of the seat surface.

The integrated control unit 30 adjusts the travel state by reflecting the weight shift and the gravity center change, which were detected by the posture sensing unit 60, in the current operation instruction detected by the operation unit 20. In other words, when the user tilts one's upper body in accordance with the travel direction while operating the operation unit 20 while traveling, because corresponding weight shift and gravity center change of the seat surface will occur, it will be possible to further approximate the user's intended travel state.

Meanwhile, when the user starts swaying one's upper body forward and backward or leftward and rightward while traveling, or when the user tilts one's upper body only in a specific direction for a long time, it is possible to determine that the user may have suffered a cerebral nervous illness or a heart attack.

Furthermore, the integrated control unit 30 (speech analysis unit) analyzes a spoken content based on the user's voice collected via the directional microphone 35, and adjusts the travel state based on the analysis result. In other words, by reflecting the spoken content related to travel instructions among the user's spoken content, it will be possible to approximate the user's intended travel state.

For example, even when the user has numbness in one's finger while traveling or when the operation unit 20 malfunctions, the user can immediately stop the mobility 2 based on a spoken content to such effect.

Furthermore, the mobility 2 comprises a physiological state detection unit 61 which detects a physiological state of the user, and, when the physiological state detected by the physiological state detection unit 61 is outside of a predetermined standard range for a predetermined time or longer, the integrated control unit 30 adjusts the current travel state of the mobility 2 to a travel state which gives priority to ensuring safety irrespective of the current operation instruction detected by the operation unit 20.

As the physiological state, used may be blood pressure, arteriosclerosis, electrocardiac, breathing, swallowing, sleeping or the like. When giving consideration to the user's convenience in getting in or out of the mobility 2, it is desirable to equip the mobility 2 with a non-invasive measurement means which uses light or laser.

As a non-invasive blood pressure measurement method, applied may be the blood flow-based blood pressure calculation device described in International Application No. 2015/068787 by the present inventors. Moreover, as a non-invasive blood flow measurement method and arteriosclerosis measurement method, applied may be an optical non-contact vascular state measurement device described in Patent Registration No. 5283700 by the present inventors. Furthermore, as a method of measuring brain waves or brain activity, applied may be the brain wave detection device based on the cephalic blood flow measurement described in Patent Registration No. 5717064 and Patent Registration No. 5295584 by the present inventors.

Consequently, if it is determined that the user's physiological state is inferior and may impair the travel and movement of the mobility 2, it will be possible to avoid any subsequent risks by forcibly guiding the mobility 2 to a place where safety can be ensured.

By simultaneously warning those around the mobility 2 by emitting an emergency alert from a speaker 36 provided to the mobility 2 or sending emergency information to a portable terminal held by the user's interested party via a communication function, the function for protecting the user can be fulfilled.

Furthermore, the mobility 2 includes an armrest part 12 and an incidental display unit 62 such as a monitor which notifies the user, in real time, either one or both of a content of adjustment and a fact of adjustment of the travel state adjusted by the integrated control unit 30. Consequently, the user can recognize the content of adjustment or fact of adjustment of the travel state in the form of feedback.

Furthermore, the mobility 2 includes, in addition to or in substitute for the display unit 62, a stimulation application unit 63 as an information content notification unit which comes into contact with the user's body surface and applies physical (mechanical, electric and/or thermal) stimulation. The integrated control unit 30 notifies the user, in real time, either one or both of the content of adjustment and the fact of adjustment of the travel state by controlling the stimulation application unit 63 and applying stimulation to the user's body at a predetermined timing and a predetermined pattern.

Consequently, the user can recognize the content of adjustment or fact of adjustment of the travel state in the form of feedback, and acquire a learning effect based on function recovery by being aware of the difference between one's own operation instruction and the adjustment that was made.

Furthermore, the mobility 2 includes a position information transmission unit 64 configured from a GPS (Global Positioning System) which transmits the position information of the mobility 2, and the information communication unit 50 transmits the current position information obtained from the position information transmission unit 64. Consequently, with the mobility system 1, the external data terminal device 4 will also be able to constantly confirm the position information of the mobility 2.

Furthermore, with the mobility system 1, the data terminal device 4 sends a command signal representing an operation command which was externally input to the mobility 2, and, upon receiving the command signal via the information communication unit 50, the integrated control unit 30 (operation adjustment unit) of the mobility 2 preferentially switches to a travel state according to the operation command based on the command signal irrespective of the current operation instruction.

Consequently, with the mobility system 1, when the administrator using the data terminal device 4 wishes to bring over the mobility 1 in cases where there is concern regarding the health of the user riding the mobility 2, the administrator can change the destination of the mobility 2 to one's own location and forcibly operate and cause the mobility 2 to travel to one's own location. Otherwise, as a result of the administrator, who is using the data terminal device 4, remotely controlling the mobility 2, it will be possible to sufficiently ensure safety even when the user riding the mobility is a person who requires nursing care.

(4) Method of Ensuring Safe Travel Path in This Embodiment

The mobility 2 is configured to recognize an approaching target object by using an imaging unit which captures images from a plurality of different viewpoints and, by calculating the relative position of the target object and the mobility body, determines whether the approaching target object within a predetermined target distance is an object to which the mobility 2 should be approaching, or an obstacle.

In this embodiment, a stereo camera (not shown) may be used as the imaging unit in substitute for the RGB-D sensor 32. While the stereo camera, as with the RGB-D sensor 32, is also a device capable of simultaneously acquiring depth information and images, because an error will occur in the depth information with the RGB-D sensor 32 which uses infrared rays in a general household environment due to the influence of sunlight, it is desirable to use a stereo camera which is not affected much by sunlight.

Depending on the household environment, it is necessary to capture images across the entire long side of the target object, and, in particular, because furniture such as a bed has a length of roughly 2 m, the distance required for capturing images of the entire bed will be shorter as the viewing angle of the camera is broader, and the limiting conditions of the dimensions of the room are alleviated. As a camera that satisfies the foregoing conditions, for instance, used may be the ZED 2K stereo camera manufactured by STEREOLABS.

When this stereo camera is applied, because the maximum viewing angle is 110 degrees, distance can be measured from 70 cm to 20 m, and the overall image of the bed can be captured from a position that is approximately 80 cm away from the bed.

Note that, with the mobility of this embodiment, the stereo camera is placed above the backrest part so that the user and the mobility body will not be in the line of sight of the stereo camera. Moreover, the coordinate system of the mobility and the coordinate system of the stereo camera are matched in advance.

By using the coordinates of a region where an object is captured within the frame of the stereo camera, the XYZ coordinates of that object in the camera coordinate system are acquired. The coordinates (x, y) in which the upper left pixels within the frame of the region where the object is captured as the origin and the element i of the one-dimensional array representing a 3D image has the relation shown in following Formula (1) by using a weight vector w.

[Math 1]

$$i = w*y + x \qquad (1)$$

By using this Formula (1), it becomes possible to match the coordinates in the camera frame and the coordinates on the 3D image one-on-one, and, by designating a region within the camera frame, the XYZ coordinates of that region in a camera coordinate system can be acquired.

In the mobility 2, the integrated control unit 30 foremost acquires an RGB image from the stereo camera, and performs depth calculation processing by using disparity information. Next, after performing object recognition based on a learning model, the integrated control unit 30 performs coordinate calculation processing of the target object in the camera coordinates. Finally, the integrated control unit 30 generates an output signal for autonomously moving the mobility 2 to the destination, and sends a command to the travel control unit 41. The travel control unit 41 operates the travel drive unit 15 based on the given command.

Here, in order to support movement in daily living, consideration must be given to use in a general household. Depending on the household, because various types of furniture such as a bed, a desk, and a chair are used, it is necessary to perform general object recognition.

Thus, the integrated control unit 30 creates a recognition model for use in a general household environment by using machine learning as the method of discriminating the target object from the RGB image data. Because general object recognition is a classification problem of the image, a convolutional neural network (CNN) is used. CNN has a plurality of convolution layers and a pooling layer (compressive layer) arranged alternately with the convolution layer, and, by superimposing the local characteristics of the RGB image data in a hierarchical manner, the image can be classified accurately.

CNN is one structure of the neural network in which a convolution layer for analyzing an image of input data, while maintaining the shape thereof, and detecting a pattern within the image based on the convolution of the image, and a pooling layer having a function of reducing the positional sensitivity of the extracted characteristics by compressing the number of pixels in the vertical and horizontal directions, are added in front of all bonding layers containing the bonds between all neurons of adjacent layers.

Figure 3B:
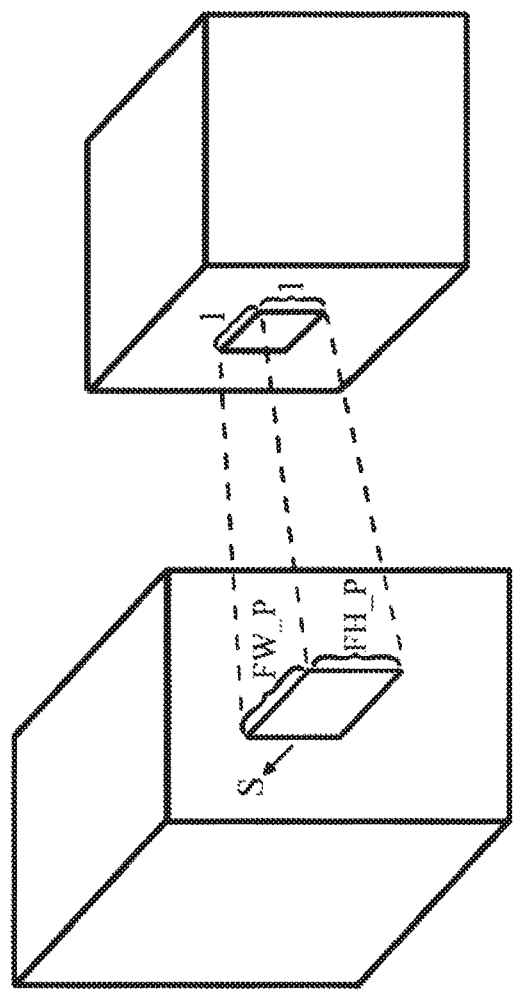
FIG. 3B is a conceptual diagram explaining the convolution layer and the pooling layer of the convolutional neural network.

Conceptual diagrams which visualize the processing performed in the convolution layer and the pooling layer are shown in FIG. 3(A) and FIG. 3(B), respectively. In FIG. 3(A), number of channels is C, height is H, and width is W with regard to the input image, and number of channels is C, height is FH_C, and width is FW_C with regard to the filter. The convolution processing of multiplying and adding the corresponding elements of the input image and the filter is performed in each channel, and the value obtained by adding the calculation results of each channel is output.

Thus, the number of channels of output data will be 1. The convolution processing is performed in all regions of the input image by using a stride S, which is a value for defining the extent of shifting the filter. The height OH and width OW of the output data will be as shown in following Formula (2) and Formula (3), and become the input data of the subsequent layer.

[Math 2]

$$OH = \frac{H + 2P - FH\_C}{S} + 1 \qquad (2)$$

[Math 3]

$$OW = \frac{W + 2P - FW\_C}{S} + 1 \qquad (3)$$

In FIG. 3(B), the filter size of performing the pooling processing was set as height FH_P and width FW_P. In the pooling processing, there is Max-Pooling which uses the maximum value included in the region as the output, and Average-Pooling which returns the average value of the region. Because only one value is returned for each region, the output channel will be height 1 and width 1. The filter is shifted in the length of the stride S, and this processing is performed in all regions of the input image.

Figure 4:
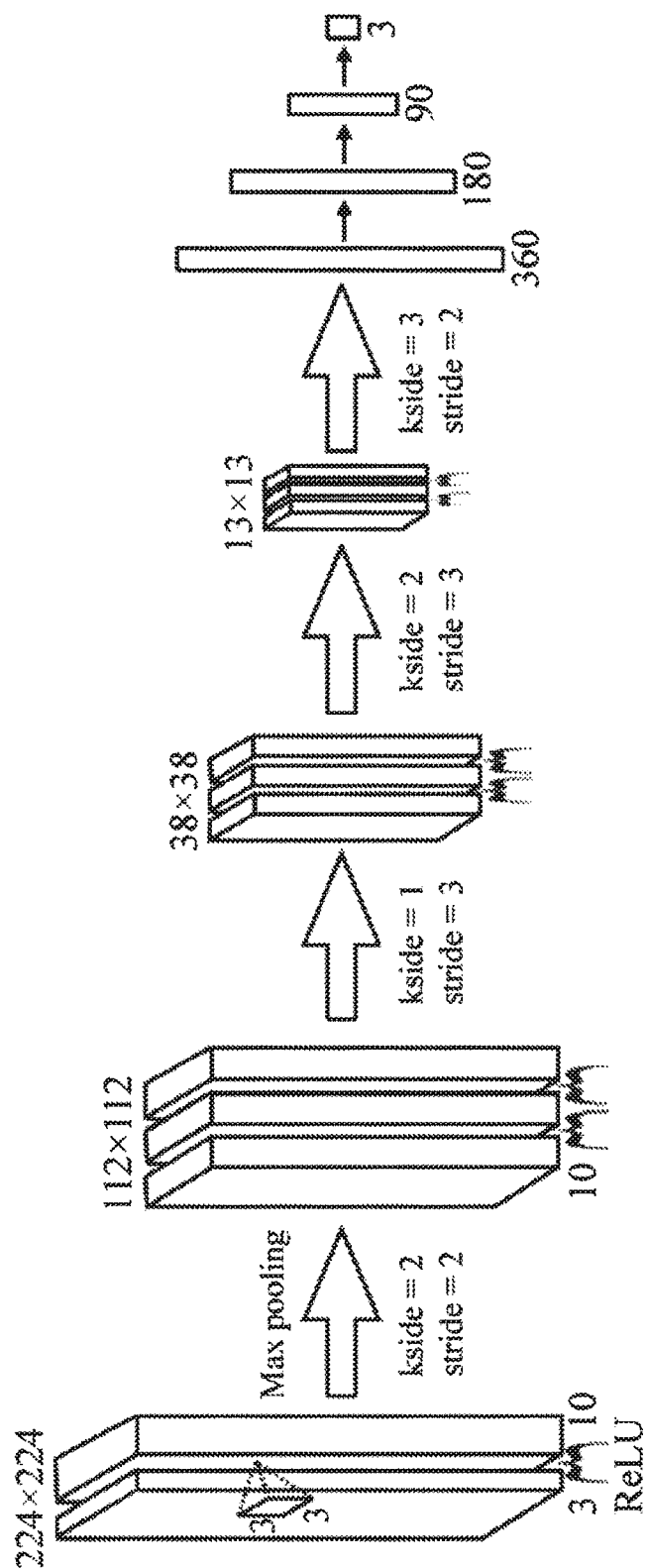
FIG. 4 is a conceptual diagram showing the structure of the learner created in the convolutional neural network.

FIG. 4 shows a structure of the created learner. The structure of the created learner was configured by referring to the neural network obtained by superimposing 10 or more layers of CNN configured from the convolution layer and pooling layer referred to as a VGB model by Oxford University.

With this learner, the input corresponds to an image of 224×224, the stride S is 1, and the filter is 3×3. Moreover, padding of satisfying only the width designated around the image with 0 is performed. Consequently, because following Formula (4) is satisfied, it is evident that the image is not compressed in the convolution layer.

[Math 4]

$$OH = OW = \frac{224 + 2 \cdot 1 - 3}{1} + 1 = 224 \qquad (4)$$

Moreover, the pooling layer compresses the input image and uses the result as the output signal with padding as 0 m, filter size as ksize, and stride as the value indicated below the arrow. Here, a ReLU (Rectified Linear Unit) is used as the activation function. In order to create a learning model, 800 images of a bed, 800 images of a desk and 800 images of a chair (total of 2,400 images) were used from the image database ImageNet, and RGB images obtained by resizing images having a size of 224×224 were prepared. Among these images, 1,800 images were used as training data, and 600 images were used as test data. Training data is used in the learning for determining the parameters of CNN.

Test data is used for sequentially evaluating the recognition rate of the created learning model. The loss function for obtaining the loss rate to be used as the index indicating the learning status is represented by using the Softmax function and cross entropy error. The Softmax function is frequently used in the classification problem, and can be expressed as shown in following Formula (5) when the output that is ultimately obtained from the neural network is $y_k$, input signal is $a_k$, and number of layers of the output layer is n.

[Math 5]

$$y_k = \frac{e^{a_k}}{\sum_{i=1}^{n} e^{a_k}} \quad (5)$$

By using this Formula (4), the sum of outputs will be 1, and the output value obtained from the Softmax function can be treated as the probability. Moreover, the cross entropy error can be expressed as shown in following Formula (6). $t_k$ is training data in which the index used as the correct answer label is expressed as 1, and others are expressed as 0.

[Math 6]

$$E = -\sum_{k} t_k \log_e y_k \quad (6)$$

The learning of parameters is performed so that this loss rate will decrease. According to a learner created using CNN having the function of the parameters of the learning model, the final recognition rate of the training data and the test data upon performing learning by using the training data was approximately 90% and approximately 94%, respectively. This recognition rate is a value which expresses, in percentage, the possibility that the output result is a correct answer relative to the label of all recognition targets.

Because there is no significant difference between the recognition rate of the training data and the recognition rate of the test data as described above, it can be understood that learning can be performed without causing any excessive learning.

Figure 5:
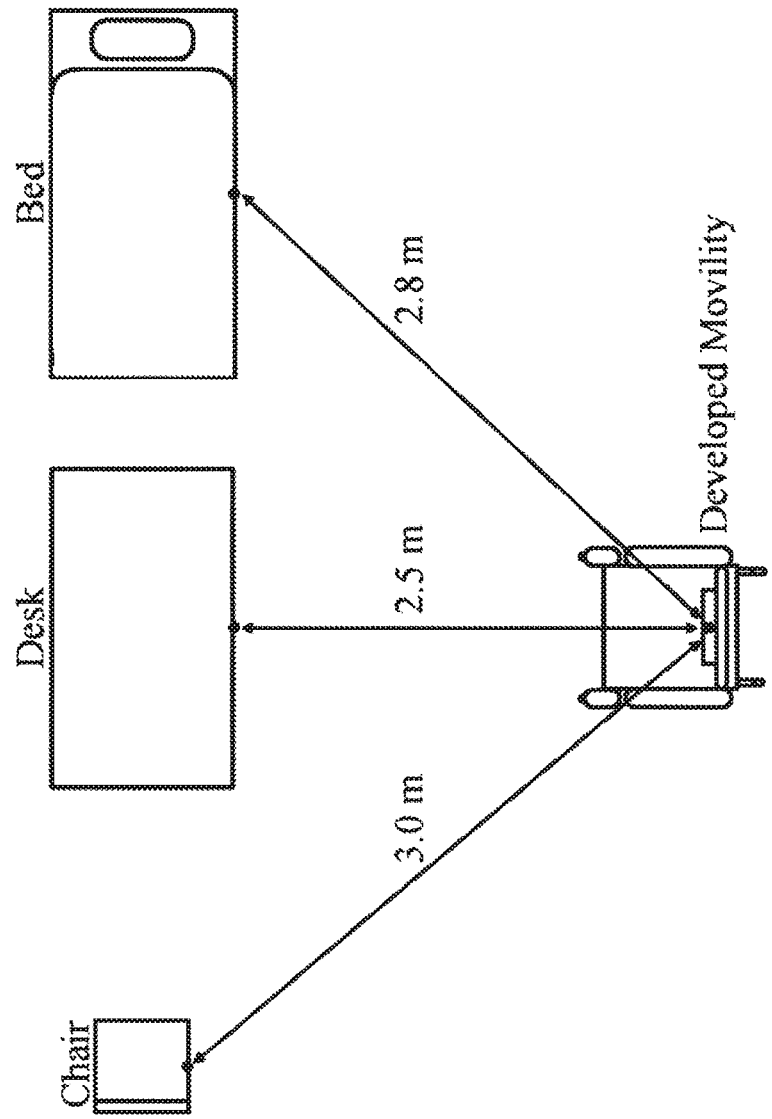
FIG. 5 is a diagram showing the test environment related to the recognition method of the target object.

A bed, desk and chair were hypothesized as the target objects to be recognized in actual indoor movement, and the foregoing recognition method of target objects using the learning model was adopted. As shown in FIG. 5, the recognition targets are arranged so that the overall image of all recognition targets will appear within the recognition range and the recognition range and the center of the recognition targets will coincide.

In this test, recognition of each target object was performed 15 times from the images of the recognition targets that were prepared in advance. Based on the recognition results from the foregoing recognition method, the relative position of the mobility and the target object is calculated, and the fact that the mobility can autonomously approach the target object up to the target distance is confirmed.

The recognition rates of the bed, desk and chair obtained as the test results are respectively shown in FIG. 6 to FIG. 8. Based on these results, it was confirmed that the recognition method of target objects according to the present invention can be sufficiently used on a practical level.

Figure 9:
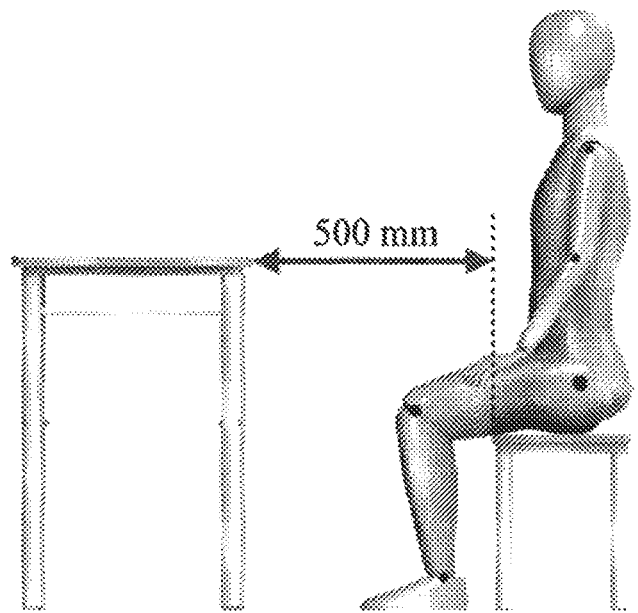
FIG. 9 is a schematic diagram explaining the distance between the front edge of the seat surface and the target object.

Subsequently, a performance evaluation test of the autonomous mobile function of moving to the target object is performed. When the range that the user can reach (touch) the target object is the target distance, the 5 percentile value of the upper limb length of men and women who are 60 years of age or older is roughly 60.8 cm, and, for the hand of users of the 5 percentile value to reach the target object, the front edge of the seat surface of the mobility must approach the target object at a distance of 60 cm or closer. Furthermore, as a result of giving consideration to the user grabbing the target object to get on the mobility after reaching the target object, the target distance between the front edge of the seat surface of the mobility and the target object is set to be 50 cm or less. FIG. 9 shows a state where the distance between the front edge of the seat surface and the target object is 50 cm.

The test environment is the same as in the function evaluation test of the foregoing recognition method, and the test is conducted 5 times each for the bed, desk, and chair. The distance between the front edge of the seat surface of the mobility and the target object was measured using a measure.

Figure 10:
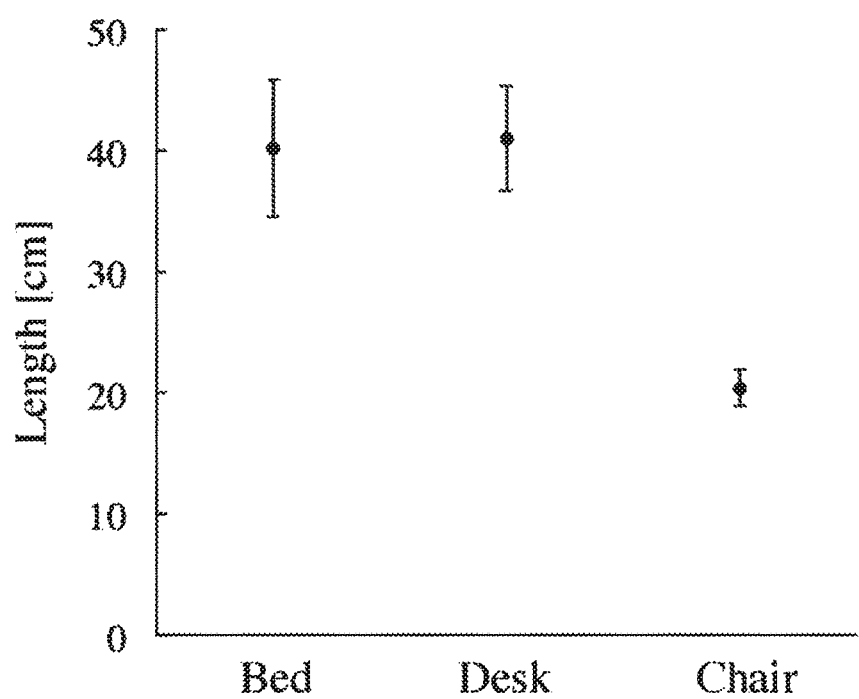
FIG. 10 is a diagram showing the average distance and standard deviation between the front edge of the mobility seat surface after movement and the target object.

FIG. 10 shows the average and standard deviation of the distance between the front edge of the seat surface of the mobility after movement and the target object. According to these results, it was confirmed that the front edge of the seat surface of the mobility could approach the target object up to 50 cm as the target in all tests.

Accordingly, in the mobility of the present invention, the target object is recognized based on the RGB image data, which is the imaging result of the stereo camera (imaging unit), and whether the target object has approached to be within a predetermined target distance is an obstacle is determined while calculating a relative position of the target object and the mobility body based on depth data calculated from the RGB image data.

Consequently, the mobility 2 can recognize whether the approaching target object is an obstacle according to the circumstances and generate a safe travel path and engage in autonomous travel based on the relative position of the target object and the mobility body.

(5) Other Embodiments

Note that, while the foregoing embodiment explained a case where a two-wheel drive four-wheel mobile object capable of traveling according to external operations or autonomously was used as the mobility 2; that is, a case of configuring the travel drive unit 15 from the driving rear wheels 13a, 13b, the front wheels 14a, 14b, the motor drivers 42a, 42b and the drive motors 43a, 43b, the present invention is not limited thereto, and a four-wheel drive four-wheel mobile object may also be used as the mobility 2, and so as long as the user can travel in a state of being safely seated, various types of driving methods and number of wheels may be adopted. Moreover, various traveling mechanisms such as caterpillars and omni wheels, other than wheels, may also be adopted.

Moreover, while the foregoing embodiment explained a case where the SLAM technology based on the laser range sensor 31, the RGB-D sensor 32 and the 3D distance image sensor 33 was applied as the environment sensing unit on the body side of the mobility 2 for sensing the travel environment while traveling, the present invention is not limited thereto, and various means such as the imaging camera 34 and the directional microphone 35, or the combinations thereof, may also be adopted so as long as it is possible to comprehend the travel environment of the mobility 2 while traveling.

Furthermore, while the foregoing embodiment explained a case where the display unit 62 and the stimulation application unit 63 were applied as the information content notification unit, the present invention is not limited thereto, and various means such as the speaker 36 and the display unit 62, or the combinations thereof, may also be adopted so as long as it is possible to allow the user to sense stimulation in the form of feedback.

Furthermore, while the foregoing embodiment explained a case where, as the information acquisition unit for acquiring environmental information from the environmental information provision unit 3, the imaging camera 34 was applied in the case of vision information, the information communication unit 50 was applied in the case of electromagnetic information and radio wave information, and the directional microphone 35 was applied in the case of sound information, the present invention is not limited thereto, and various types of acquisition means may be adopted so as long as it is possible to acquire various types of environmental information in response to a request from the mobility or automatically upon nearing the target location.

REFERENCE SIGNS LIST

1 . . . mobility system, 2 . . . mobility, 3 . . . environmental information presentation unit, 4 . . . data terminal device, 5 . . . management server, 6 . . . communication line, 10 . . . seat part (support part), 11 . . . backrest part, 12 . . . chair part, 13*a*, 13*b* . . . driving rear wheel, 14*a*, 14*b* . . . front wheel, 15 . . . travel drive unit, 20 . . . operation unit, 21 . . . biosignal detection unit, 30 . . . integrated control unit, 31 . . . laser range sensor, 32 . . . RGB-D sensor, 33 . . . 3D distance image sensor, 34 . . . imaging camera, 35 . . . directional microphone, 36 . . . speaker, 40 . . . target travel route storage unit, 41 . . . travel control unit, 42*a*, 42*b* . . . motor driver, 43*a*, 43*b* . . . drive motor, 50 . . . information communication unit, 60 . . . posture sensing unit, 61 . . . physiological state detection unit, 62 . . . display unit, 63 . . . stimulation application unit, 64 . . . position information transmission unit.

The invention claimed is:

1. A mobility including an operation unit which detects an operation instruction input by a user, and a travel drive unit which drives and causes the mobility to travel at a travel speed and in a travel direction according to the operation instruction detected by the operation unit, comprising:
 a biosignal detection unit including an electrode for detecting a biosignal of the user from the user's finger which comes into contact with the operation unit;
 a voluntary control unit which generates a command signal for causing the travel drive unit to generate power according to the user's intention based on the biosignal acquired by the biosignal detection unit;
 an environment sensing unit which enables the mobility body side to sense a travel environment during travel;
 an information acquisition unit which acquires at least one or more types of environmental information presented from an external environment;
 a travel adjustment unit which adjusts a current travel state of the mobility to an optimal travel state for ensuring safety while reflecting the user's intention based on the current operation instruction detected by the operation unit, the command signal generated by the voluntary control unit, the travel environment sensed by the environment sensing unit, and the respective types of environmental information acquired by the information acquisition unit; and
 a travel control unit which controls the drive and travel of the mobility by the travel drive unit so as to attain the travel state adjusted by the travel adjustment unit.

2. The mobility according to claim 1, further comprising:
 a posture sensing unit which is provided at a support part for supporting a weight of the user and senses a body motion change and a gravity center change of the user,
 wherein the travel adjustment unit adjusts the travel state by reflecting the weight shift and the gravity center change detected by the posture sensing unit in the current operation instruction detected by the operation unit.

3. The mobility according to claim 1, further comprising:
 a speech analysis unit which analyzes a spoken content based on the user's voice collected via a directional microphone,
 wherein the travel adjustment unit adjusts the travel state by reflecting the analysis result of the speech analysis unit in the current operation instruction detected by the operation unit.

4. The mobility according to claim 1, further comprising:
 a physiological state detection unit which detects a physiological state of the user,
 wherein, when the physiological state detected by the physiological state detection unit is outside of a predetermined standard range for a predetermined time or longer, the travel adjustment unit adjusts the current travel state of the mobility to a travel state which gives priority to ensuring safety irrespective of the current operation instruction detected by the operation unit.

5. The mobility according to claim 1,
 wherein the environment sensing unit includes an imaging unit which captures images of a target object from a plurality of different viewpoints, and
 wherein the travel adjustment unit recognizes the target object based on RGB data, which is an imaging result of the imaging unit, and determines whether the target object which has approached to be within a predetermined target distance is an obstacle while calculating a relative position of the target object and the mobility body based on depth data calculated from the RGB image data.

6. The mobility according to claim 1, further comprising:
 an information content notification unit which notifies the user, in real time, either one or both of a content of adjustment and a fact of adjustment of the travel state adjusted by the travel adjustment unit.

7. The mobility according to claim 6,
 wherein the information content notification unit is configured from a stimulation application unit which applies physical stimulation to the user according to the content of adjustment of the travel state adjusted by the travel adjustment unit.

8. A mobility system including the mobility according to claim 1, and an environmental information presentation unit which presents at least one or more types of environmental information to the mobility,
 wherein the environmental information presentation unit comprises:
 an information presentation unit which is provided for each type of environmental information and presents corresponding environmental information in response to a request from the mobility, and
 wherein the information acquisition unit of the mobility only acquires utilizable environmental information from each of the information presentation units.

9. The mobility system according to claim 8,
 wherein the mobility comprises an information communication unit which externally transmits the content of adjustment of the travel state adjusted by the travel adjustment unit together with at least one or more among a weight shift and a gravity center change detected by the posture sensing unit, a cognitive ability sensed by the cognitive ability sensing unit, and a physiological state detected by the physiological state detection unit, and wherein the mobility system further comprises:

a data terminal device which is provided separately from the mobility, receives various types of information sent from the information communication unit, and sends the received information to a management server via a communication line.

10. The mobility system according to claim 9, wherein the mobility further comprises a position information detection unit which detects position information of the mobility, and wherein the information communication unit transmits the current position information obtained from the position information transmission unit.

11. The mobility system according to claim 9, wherein the data terminal device sends a command signal representing an operation command which was externally input to the mobility, and wherein, upon receiving the command signal via the information communication unit, the operation adjustment unit of the mobility preferentially switches to a travel state according to the operation command based on the command signal irrespective of the current operation instruction.

\* \* \* \* \*